United States Patent
Lewis et al.

(10) Patent No.: US 11,510,708 B2
(45) Date of Patent: Nov. 29, 2022

(54) THORACOLUMBAR PLATE WITH CAM LOCK

(71) Applicants: Adam Isaac Lewis, Madison, MS (US); Chase Thornburg, Cumming, GA (US)

(72) Inventors: Adam Isaac Lewis, Madison, MS (US); Chase Thornburg, Cumming, GA (US)

( * ) Notice: Subject to any disclaimer, the term of this patent is extended or adjusted under 35 U.S.C. 154(b) by 0 days.

(21) Appl. No.: 17/165,281

(22) Filed: Feb. 2, 2021

(65) Prior Publication Data
US 2021/0236176 A1 Aug. 5, 2021

Related U.S. Application Data

(60) Provisional application No. 62/970,322, filed on Feb. 5, 2020.

(51) Int. Cl.
*A61B 17/70* (2006.01)
*A61B 17/84* (2006.01)

(52) U.S. Cl.
CPC ........ *A61B 17/7059* (2013.01); *A61B 17/846* (2013.01)

(58) Field of Classification Search
CPC ........ A61B 17/7058–7059; A61B 17/80–8095
See application file for complete search history.

(56) References Cited

U.S. PATENT DOCUMENTS

| | | | |
|---|---|---|---|
| 4,367,970 A | 1/1983 | Franz | |
| 5,549,612 A | 8/1996 | Yapp et al. | |
| 5,951,558 A | 9/1999 | Fiz | |
| 6,139,550 A * | 10/2000 | Michelson | A61B 17/8042 606/295 |
| 6,152,927 A | 11/2000 | Farris et al. | |
| 6,193,721 B1 * | 2/2001 | Michelson | A61B 17/1604 606/246 |
| 6,303,139 B1 | 10/2001 | Fuentes | |
| 6,383,186 B1 | 5/2002 | Michelson | |
| 6,398,783 B1 | 6/2002 | Michelson | |
| 6,527,776 B1 | 3/2003 | Michelson | |
| 6,620,163 B1 | 9/2003 | Michelson | |
| 6,652,525 B1 | 11/2003 | Assaker et al. | |
| 6,669,700 B1 | 12/2003 | Farris et al. | |
| 6,793,658 B2 * | 9/2004 | LeHuec | A61B 17/808 606/86 B |
| 6,890,335 B2 * | 5/2005 | Grabowski | A61B 17/7059 606/71 |
| 6,926,718 B1 | 8/2005 | Michelson | |

(Continued)

*Primary Examiner* — Eduardo C Robert
*Assistant Examiner* — Steven J Cotroneo
(74) *Attorney, Agent, or Firm* — David L. King

(57) ABSTRACT

A plate assembly for engaging at least two vertebral bodies of a human spine along the anterior aspect of the spine has a plate and at least two cam locks. The plate has a lower surface for contacting the vertebral bodies and an upper surface opposite to said lower surface. The plate assembly has a plurality of bone fastener receiving holes extending through said plate assembly from said upper surface to said lower surface. The plate has at least a first pair and second pair of said bone fastener receiving holes. The first pair is associated with a first of the vertebral bodies. The second pair is associated with a second of the vertebral bodies. A recess is associated with each of said at least first pair and second pair of said bone fastener receiving holes.

12 Claims, 9 Drawing Sheets

(56) References Cited

U.S. PATENT DOCUMENTS

| | | |
|---|---|---|
| 6,936,050 B2 | 8/2005 | Michelson |
| 6,936,051 B2 | 8/2005 | Michelson |
| 7,001,387 B2 | 2/2006 | Farris et al. |
| 7,044,952 B2 * | 5/2006 | Michelson ......... A61B 17/7059 606/282 |
| 7,077,844 B2 | 7/2006 | Michelson |
| 7,137,984 B2 | 11/2006 | Michelson |
| 7,306,605 B2 * | 12/2007 | Ross ................. A61B 17/7059 606/70 |
| 7,662,154 B2 | 2/2010 | Ribeiro |
| 7,704,255 B2 | 4/2010 | Michelson |
| 7,803,157 B2 | 9/2010 | Michelson |
| 7,875,062 B2 | 1/2011 | Lindeman |
| 8,123,788 B2 | 2/2012 | Michelson |
| 8,262,708 B2 | 9/2012 | Michelson |
| 8,277,493 B2 | 10/2012 | Farris et al. |
| 8,480,717 B2 | 7/2013 | Michelson |
| 8,641,743 B2 | 2/2014 | Michelson |
| 8,652,182 B1 | 2/2014 | Walker et al. |
| 2007/0043369 A1 * | 2/2007 | Wallenstein ....... A61B 17/8033 606/279 |
| 2007/0162013 A1 * | 7/2007 | Jacene ............... A61B 17/8042 606/288 |
| 2013/0060337 A1 * | 3/2013 | Petersheim ........ A61B 17/8042 623/17.16 |
| 2013/0204300 A1 | 8/2013 | Michelson |
| 2015/0201982 A1 * | 7/2015 | Altarac ............. A61B 17/8042 606/246 |
| 2016/0331414 A1 * | 11/2016 | Etminan ............ A61B 17/7059 |
| 2017/0056081 A1 * | 3/2017 | Langdale ............ A61B 17/725 |
| 2017/0354478 A1 * | 12/2017 | Adams .................. A61B 90/90 |
| 2018/0070992 A1 * | 3/2018 | Dabbah ............. A61B 17/7059 |

* cited by examiner

THORACOLUMBAR PLATE WITH CAM LOCK

FIELD OF THE INVENTION

The present invention relates to lateral plates generally, more specifically to thoracolumbar plate assemblies with a cam lock feature to prevent bone fasteners from loosening when installed.

BACKGROUND OF THE INVENTION

The use of anterior, cervical, lumbar or lateral plates generally is well known in the art. These plates commonly have been constructed with little concentration on providing the correct curvature profile that facilitates attachment to the vertebral bodies in the spine. As such, the surgeon is required to move more muscle material and bone tissue in order to perform a proper fit of the plate. Some plates have adequate curvature, some are provided with some curvature, most do not have the proper curvature. The thickness of the plate also plays a critical role in how well the patient recovers from the surgical procedure. Ideally the plate should be as thin as possible and yet provide as much structural support as feasible. Typically, four bone screws or fasteners are used to attach to adjacent vertebral bodies. In some cases, more than four fasteners are used, and the plate is increased in longitudinal length. To accommodate the required attachment to multiple vertebral bodies. Ideally, to keep the bone fasteners installed without backing out, locking features have been provided with these plates. These locking features typically, in almost all cases, are aligned with the axis of the holes for receiving the bone fasteners. These locking features cover a portion of the holes when installed and provide a symmetrical load upon the exterior heads, in some cases even along the sides, of the bone screws.

The present invention provides a more unique way of maintaining an asymmetric or biased force that causes the locking feature, a cam lock, to stay in position for superior holding power as described hereinafter.

SUMMARY OF THE INVENTION

A plate assembly for engaging at least two vertebral bodies of a human spine along the anterior aspect of the spine has a plate and at least two cam locks. The plate has a lower surface for contacting the vertebral bodies and an upper surface opposite to said lower surface. The plate assembly has a plurality of bone fastener receiving holes extending through said plate assembly from said upper surface to said lower surface. The plate has at least a first pair and second pair of said bone fastener receiving holes. The first pair is associated with a first of the vertebral bodies. The second pair is associated with a second of the vertebral bodies. A recess is associated with each of said at least first pair and second pair of said bone fastener receiving holes. The recess has a configuration for retaining one cam lock for locking at least two bone fasteners in each of said at least first pair and second pair of bone fastener receiving holes. The cam lock is pivotally rotatable about an axis in said recess and being offset from a transverse line passing through central longitudinal axes of each of said first or second pair of bone fastener receiving holes. The cam locks when in an open position do not cover the first pair or second pair of bone fastener holes allowing bone fasteners to be held in the bone fastener receiving holes and fastened to the vertebral bodies. Wherein rotation of the cam locks to a closed position partially covering the bone fastener receiving holes applies a downward force locking against upper surfaces of heads of the pair of bone fasteners.

In one embodiment, each cam lock has an outer perimeter having a convex arcuate curvature and a pair of opposing aligned concave arcuate curvatures. The convex arcuate curvatures define a perimeter that partially covers two bone fastener receiving holes. The opposing aligned concave arcuate curvatures when positioned between a pair of bone fastener receiving holes does not cover the holes. A portion of each cam lock adjacent the convex arcuate curvature forms a locking portion. A portion of each cam lock between the opposing aligned concave arcuate curvatures forms an arm extending from the axis of each cam lock, wherein the arm in the open position does not cover a bone fastener receiving hole. Each cam lock in the closed and locked position presses against a top portion of a bone fastener offset from the cam axis and the force causes the arm of the cam lock to tilt against a floor of the recess.

The plate has curved upper and lower surfaces. The plate curved upper and lower surfaces have a high degree of curvature similar to a L5-S1 ALIF plate. This additional curvature allows for the plate to better fit the lumbar anatomy due to the natural shape of the vertebra and lordosis of the spine similar to the L5-S1 ALIF plate.

The plate assembly further comprises fasteners of various sizes along with temporary fixation pins which can be placed into the fastener holes to assist with placing of the plate(s). The fasteners are a self-drilling and self-tapping design to eliminate additional surgical steps in the operating room setting and have a variable angle to allow for better placement due to anatomy or previously implanted devices. The bone fastener sizing is as follows: 05.0 mm, 05.5 mm, 06.0 mm with threaded lengths of one of 25, 30, 35, 40, 45, 50, or 55 mm Each bone fastener uses a robust hexalobular drive feature to prevent stripping and have a strong connecting feature to a driver so as to prevent dropping into the wound cavity or off the sterile field. The plate is sized as follows: 18 mm wide, with end to end lengths of one of 25, 30, 35, or 40 mm and approximately 3 mm thick. Diamond shaped teeth are located on the underside of each end of the lower surface of the plate to enhance grip to the bony surface.

A central cavity is located in the center of the plate to allow for alignment with a guide wire or an additional fixation screw to secure the plate to an interbody device if desired.

The plate assembly can be configured as a thoracolumbar plate assembly which can be a lateral lumbar plate, anterior plate, posterior plate, lateral plate or lumbar plate.

BRIEF DESCRIPTION OF THE DRAWINGS

The invention will be described by way of example and with reference to the accompanying drawings in which.

DETAILED DESCRIPTION OF THE INVENTION

Figure 1:
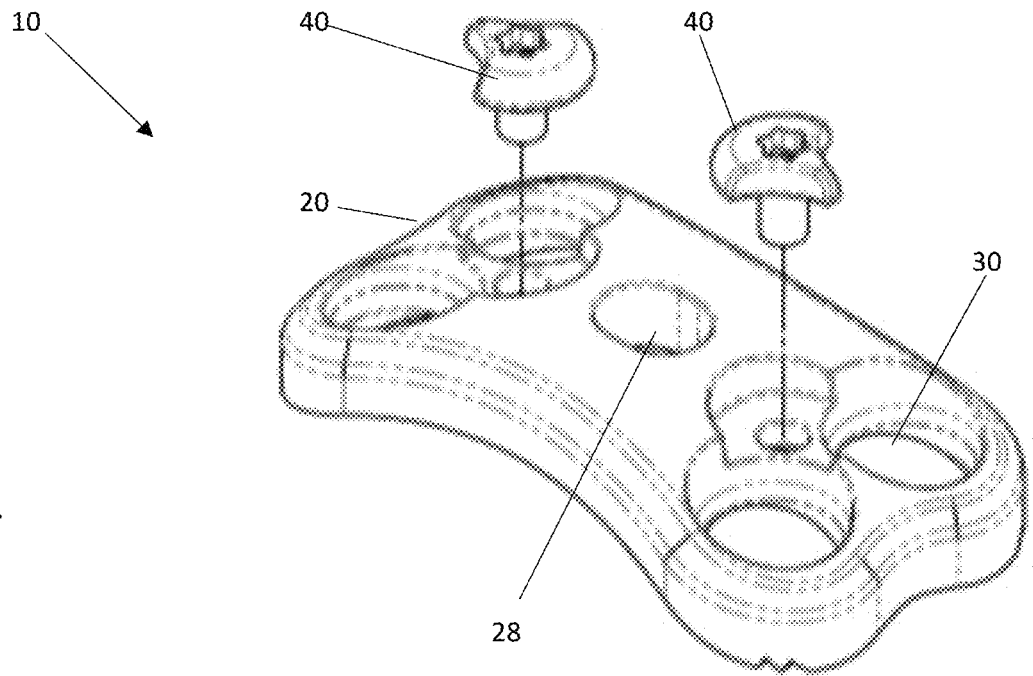
FIG. 1 is an exploded perspective view of the plate and cam locks of the present invention.
Figure 2:
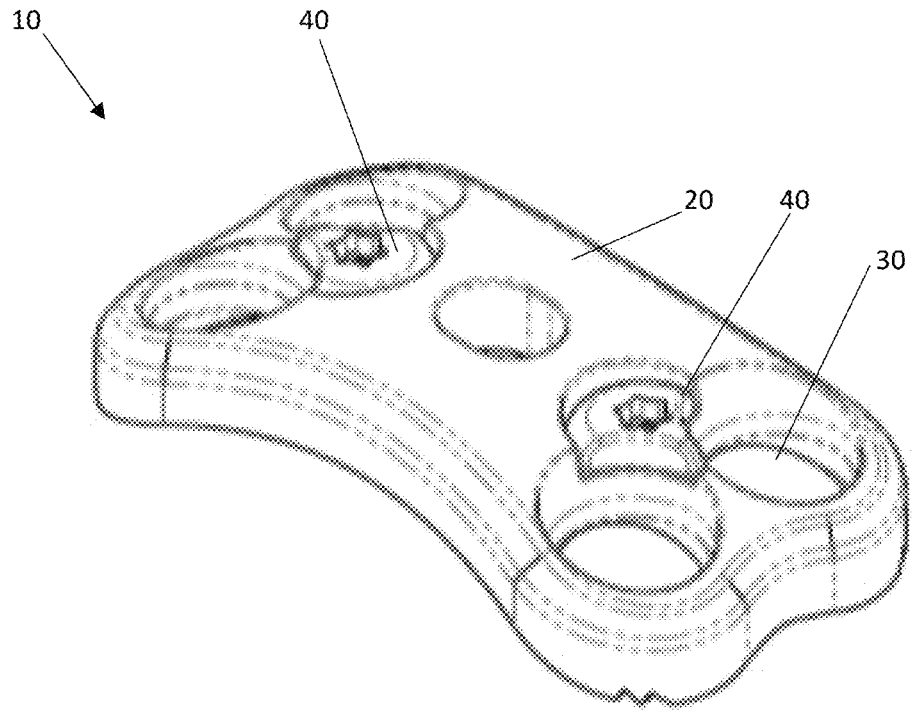
FIG. 2 is a perspective view of the assembled plate assembly with the cam locks oriented in a fully open position.
Figure 3:
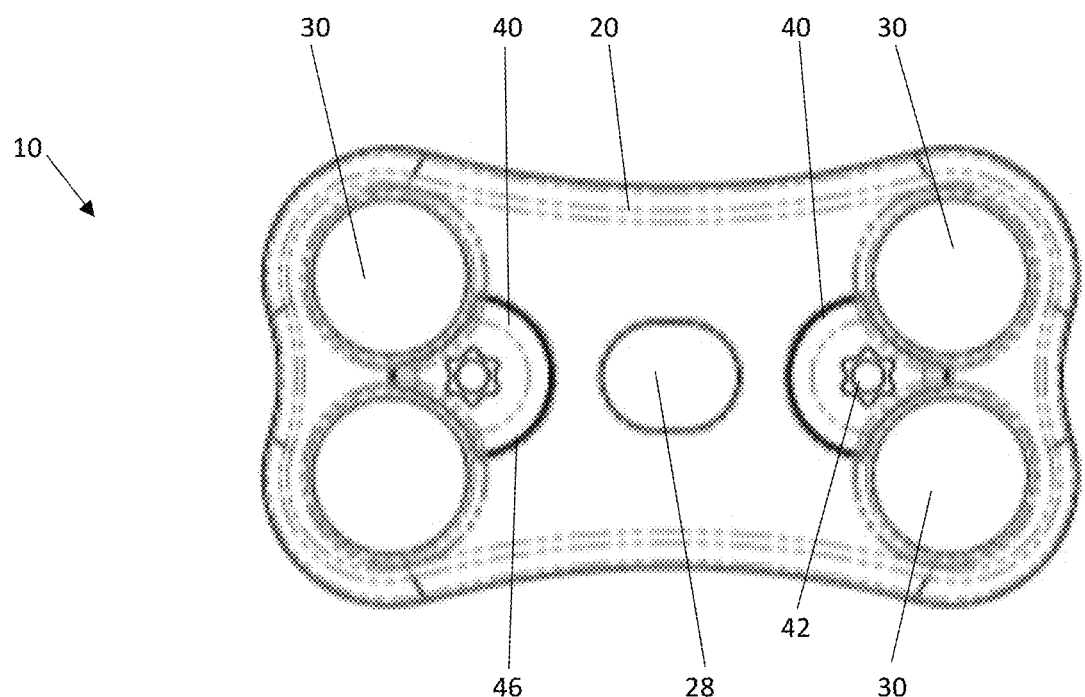
FIG. 3 is a top plan view of the plate assembly taken from FIG. 2.
Figure 4:
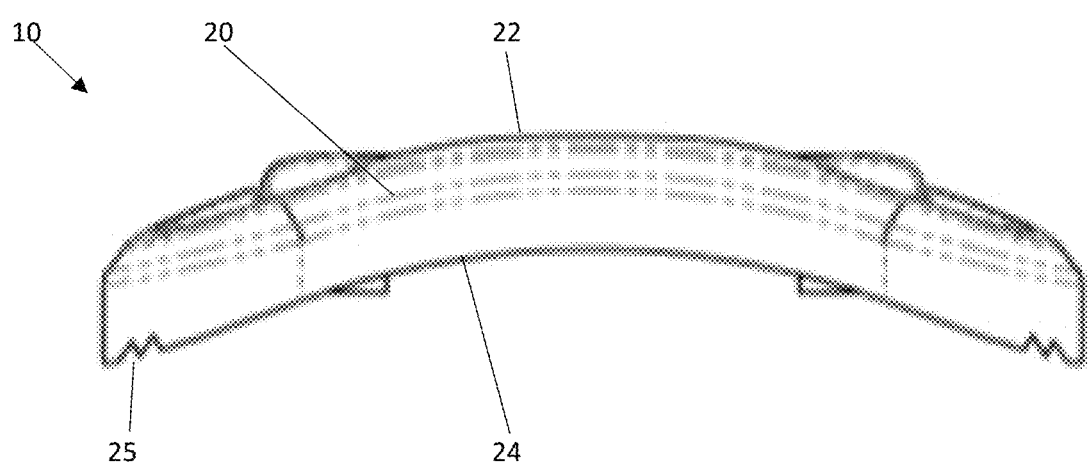
FIG. 4 is a frontal side view of the plate assembly taken from FIG. 3.
Figure 5:
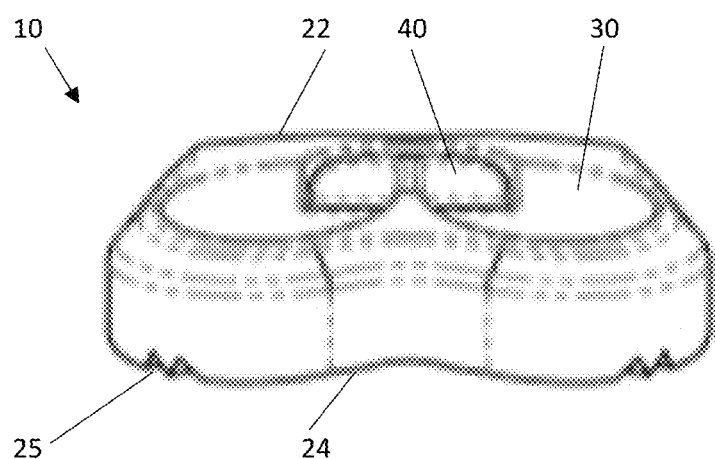
FIG. 5 is an end plan view of the plate assembly taken from FIG. 3.
Figure 6:
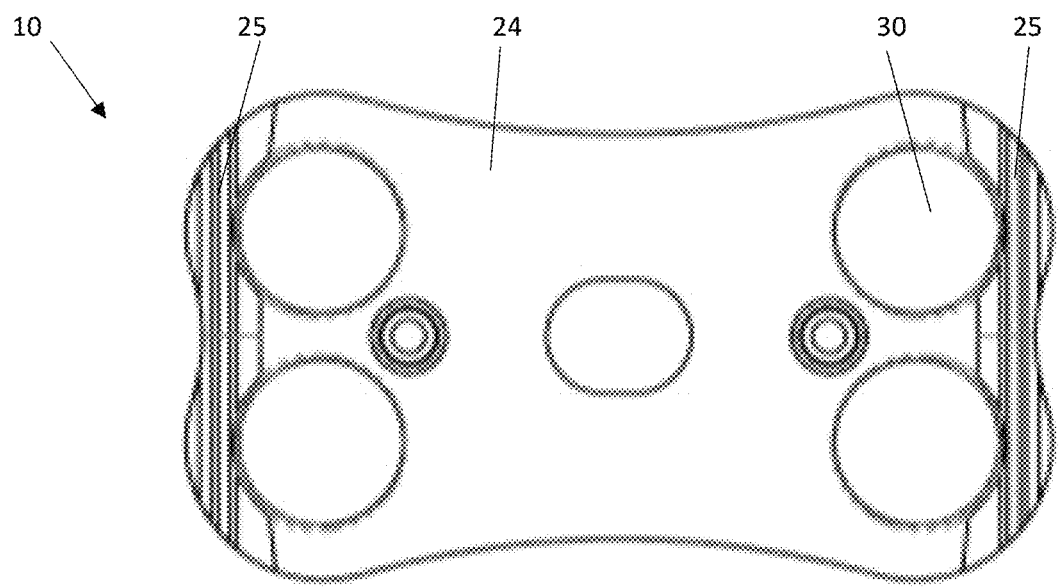
FIG. 6 is a bottom side plan view of the plate assembly taken from FIG. 3.

As shown in FIGS. 1-6, the plate 20 and cam locks 40 of the present invention plate assembly 10 are illustrated. In FIG. 1, an exploded view shows the plate 20 and a pair of cam locks 40, one at each longitudinal end of the plate 20. As shown, the cam locks 40 are positioned in the open position. In the fully open position, the bone screw or fastener receiving holes 30 are fully exposed and not covered by the cam locks 40, as illustrated in FIGS. 2 and 3. FIGS. 4-6 show the frontal end, side and bottom plane view of the plate assembly 10 taken from FIG. 3. As shown, the plate 20 has a very thin profile. The plate 20 is preferably made of titanium alloy and has a contour as described that includes both a standard curved plate as well as a plate with a higher degree of curvature similar to a L5-S1 ALIF plate. The additional curve allows for the plate to better fit the lumbar anatomy due to the natural shape of the vertebra and lordosis of the spine.

Figure 7:
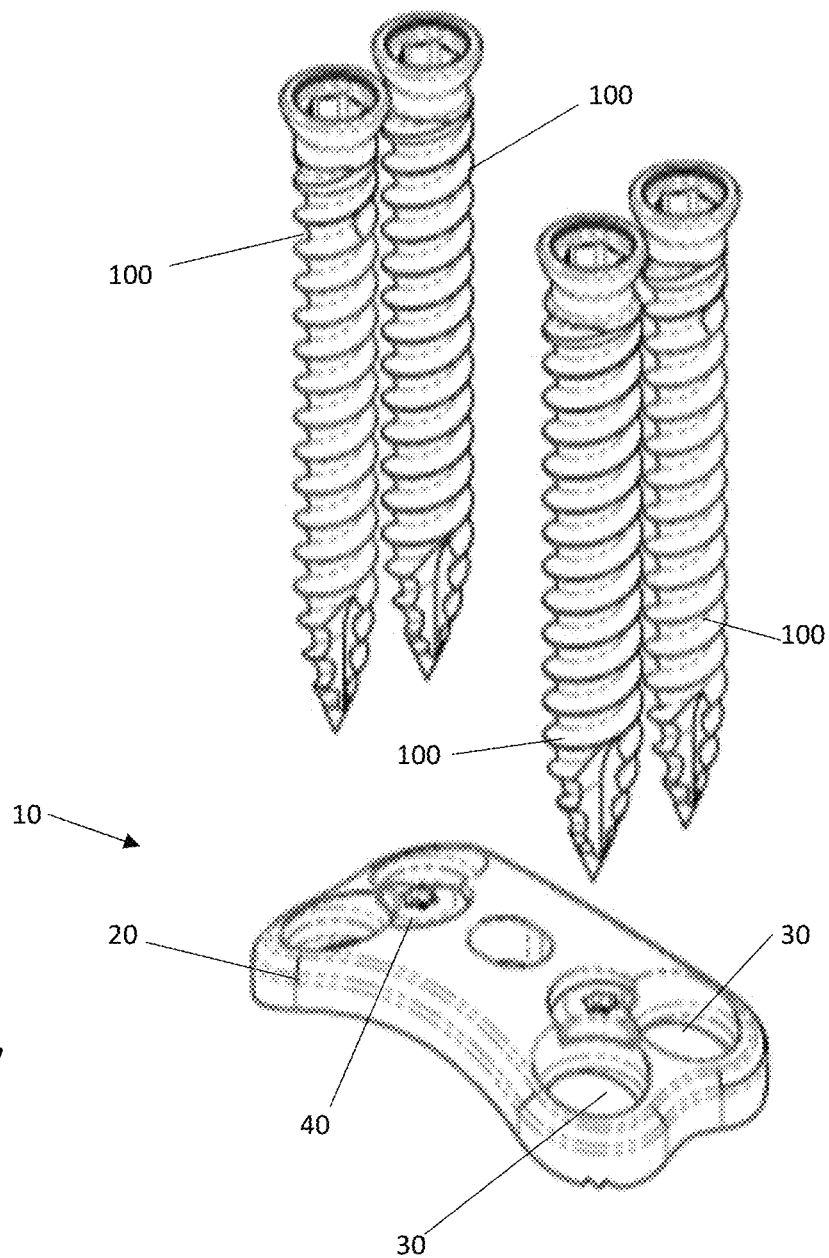
FIG. 7 is a perspective exploded view of the plate assembly with the cam locks in the fully open position and four bone fasteners positioned to be received.
Figure 8:
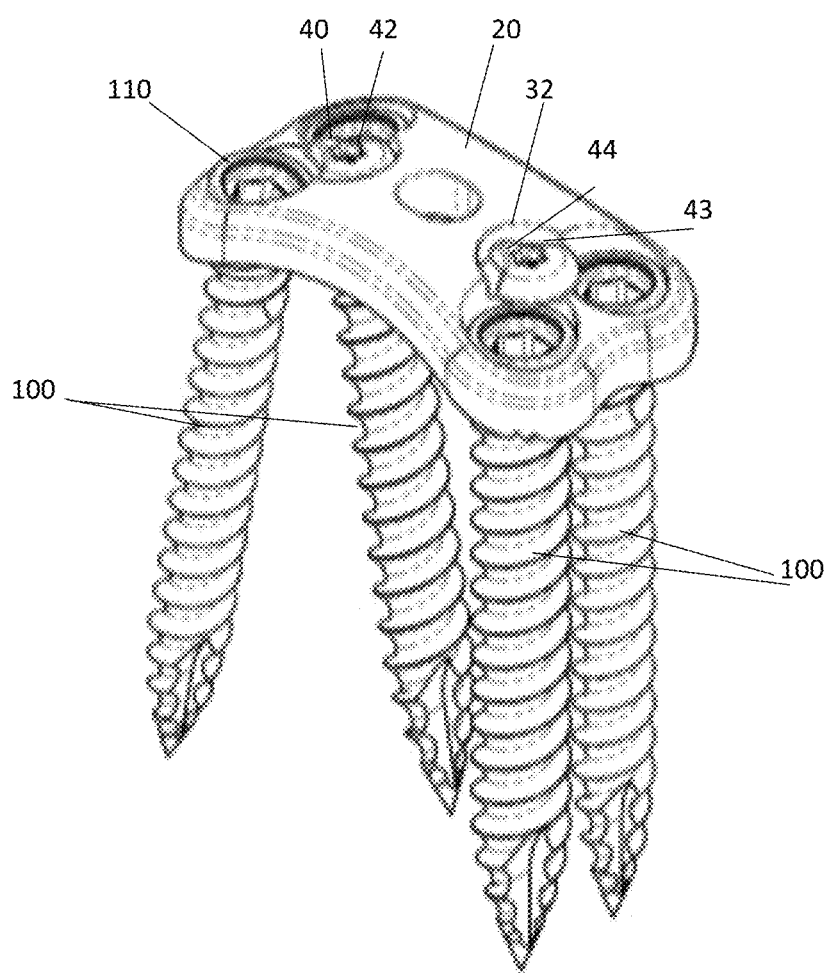
FIGS. 8-11 are views, perspective, top plan, frontal side, and end side showing the cam lock on the left in the open position and the cam lock on the right in a locked orientation wherein portions of the cam lock are covering portions of the heads of two of the bone fasteners.
Figure 9:
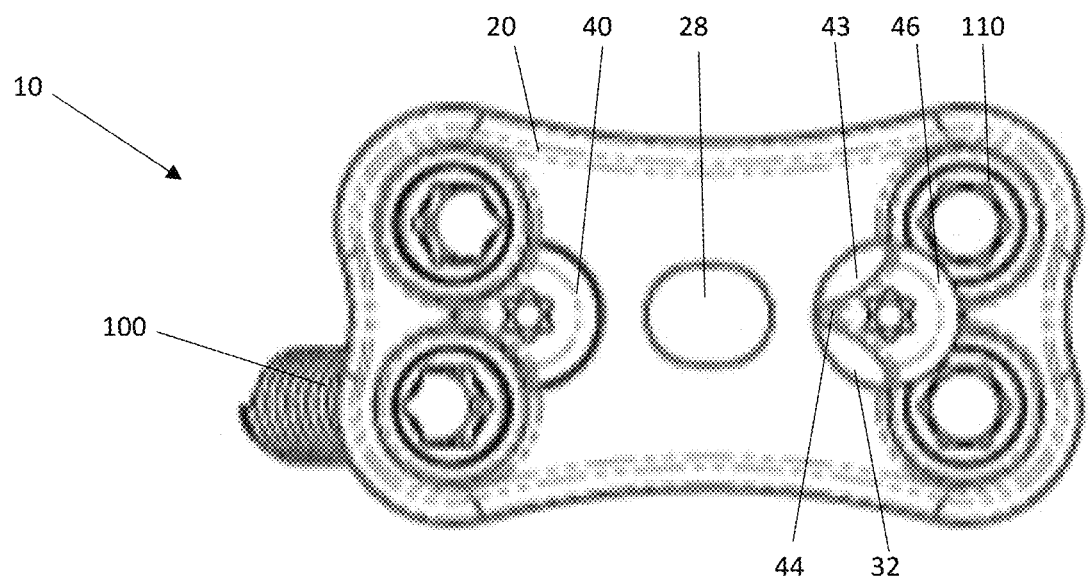
Figure 10:
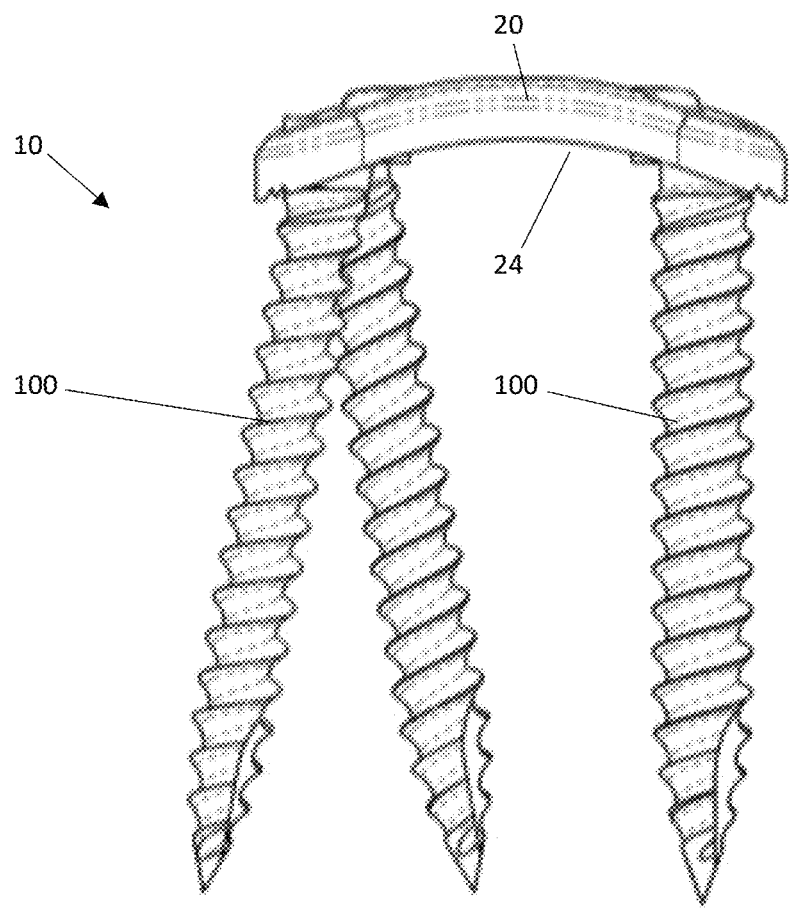
Figure 11:
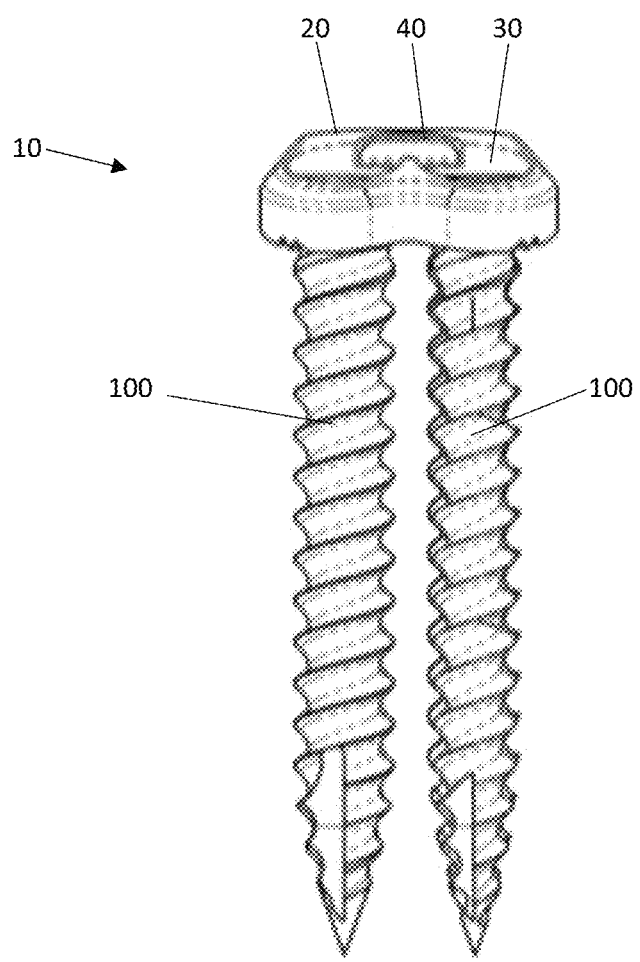

With reference to FIG. 7, a perspective exploded view of the plate assembly 10 with cam locks 40 in the fully open position shows four bone fasteners 100 positioned to be received in the bone fastener receiving holes 30.

FIGS. 8-11 are views of the bone fasteners 100 fully inserted into the bone receiving holes 30 with the cam lock 40 on the left side of the figure shown in the open unlocked position and the cam lock 40 on the right-hand side shown in the fully closed locked position where portions of the cam lock 40 cover portions of the heads 110 of two of the bone fasteners 100. As shown, the cam locks 40 have a means for inserting a driver into a driver opening 42 to turn the cam lock 40 pivotally about its axis rotating it such that the undersurface of the cam lock 40 rides against the top surface of the screw head 110 at least partially. In this orientation, when fully locked, the cam lock 40 provides a downward force on the heads 110 of the bone screws 100 that is shifted off center axis of the cam lock 40 in such a way that the opposite side of the cam lock 40 is tilted downward into a recess 32 of the plate 20, as illustrated. When this occurs, the opposite end of the cam lock 40 which is defined along the perimeter by concave surfaces 43 forms an appendage or arm 44 such that the arm 44 pushes against the bottom of the recess 32. This is unique in cam lock designs used in plates in that not only do the heads 110 of the screws 100 receive a downward force, but the opposite side of the cam lock 40 being tilted by the off axis positioning of load tends to rest against the bottom surface of the recess 32. This helps hold the cam lock 40 in position far superior to those in the prior art.

Figure 12A:
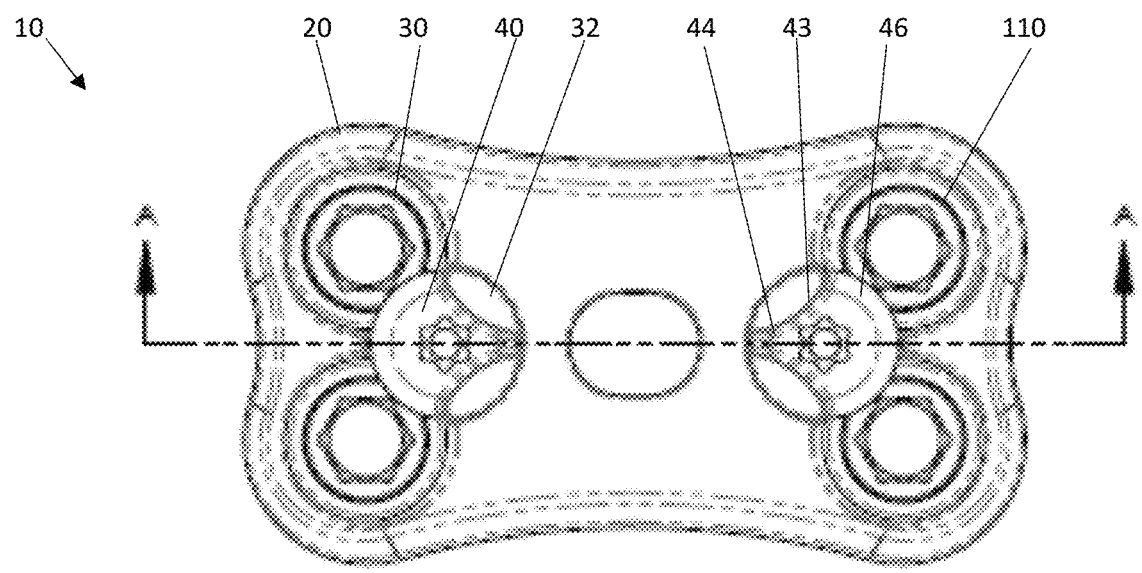
FIG. 12A is a top view of the plate assembly with the cam locks in a locked position.
Figure 12B:
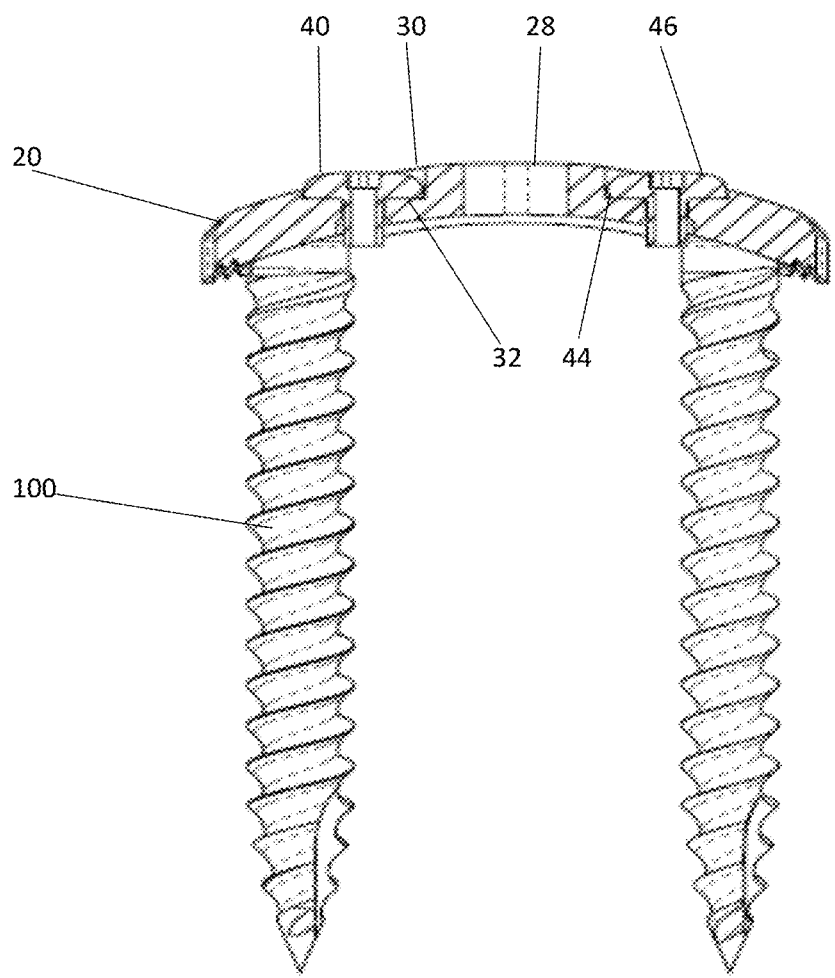
FIG. 12B is a cross sectional view taken along line A-A of FIG. 12A showing the cam lock in a locked position.

FIG. 12A is a top view of the plate assembly 10 with the cam locks 40 in a locked position. FIG. 12B is a cross sectional view taken along line A-A of FIG. 12A showing the cam locks 40 in a locked position with the arms 44 resting against the floor of the cam lock recess 32.

Figure 12C:
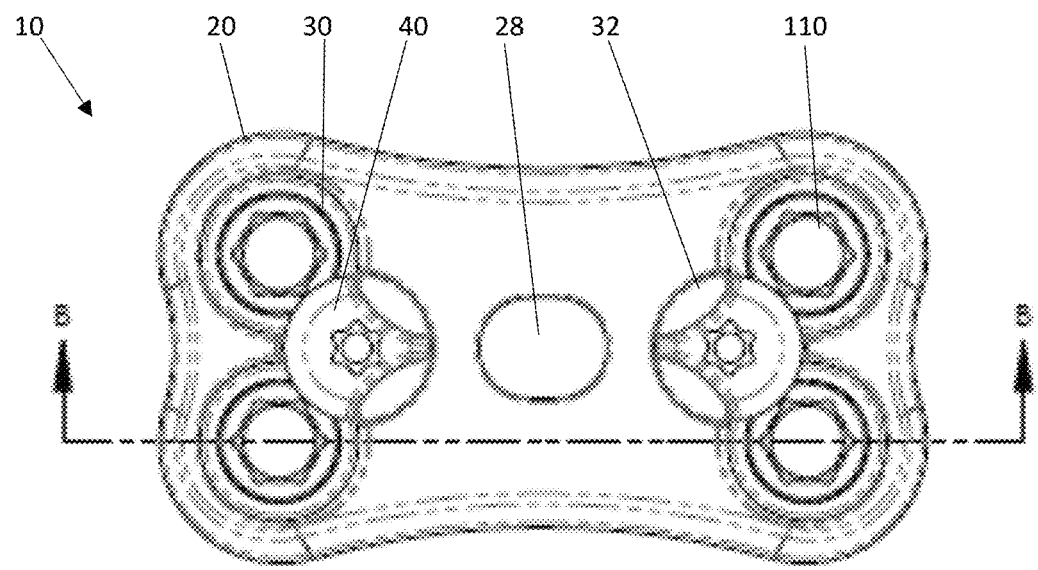
FIG. 12C is a top view of the plate assembly with the cam locks in a locked position.
Figure 12D:
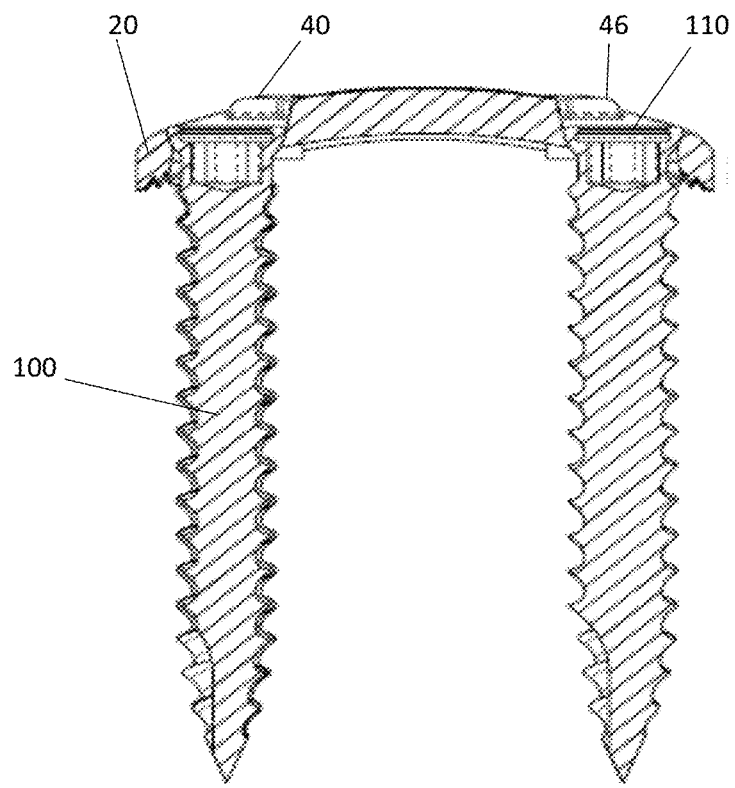
FIG. 12D is a cross sectional view along taken line B-B of FIG. 12C showing the cam lock in a locked position partially covering the heads of the bone fasteners.

FIG. 12C is another top view of the plate assembly 10 with the cam locks 40 in a locked position. FIG. 12D is a cross sectional view taken along line B-B of FIG. 12C showing the cam locks 40 in a locked position partially covering the heads 110 of the bone fasteners 100.

As illustrated, the heads 110 of the bone fasteners 100 can be provided with a means for inserting a bone fastener driver in such a way that the heads 110 of the bone fasteners 100 can be clipped on or otherwise locked to the driver during assembly. This facilitates the surgeon's ability to insert the fasteners 100 without the risk of the fasteners becoming dislodged. These features are described in a related co-pending application filed concurrently with the present application.

It is believed that the present invention provides a contoured curvature on the inner surface 24 of the plate 20 that will more closely match the contour of the spine on implantation. The plate 20 has curved upper 22 and lower 24 surfaces, the plate curved upper 22 and lower 24 surface have a high degree of curvature similar to a L5-S1 ALIF plate. This additional curvature allows the plate 20 to better fit the lumbar anatomy due to the natural shape of the vertebra and lordosis of the spine. Typically, this radius of curvature is a single radius along the longitudinal axis of the plate 20 and is approximately greater than 1.5 mm. The plate 20 is ideally suited to work with a variety of bone fasteners 100. These bone fasteners 100 can be of any particular size or shape, but preferably have an under surface on the head 110 of the bone fastener 100 that is polyaxial that allows the bone fastener 100 to be tilted in the bone fastener receiving hole 30 relative to the plate 20 in such a way that it facilitates insertion. The plate 20, additionally, on the lower surface 24 or underside at each end has diamond shaped teeth 25 located to enhance the grip to the bony surface of the spine. A central cavity 28 is located in the center of the plate 20 to allow for alignment with a guide wire or an additional fixation screw to secure the plate 20 to an interbody device if desired.

As mentioned above, the bone fasteners 100 are adapted to fit into a hole 30 below the outer surface 22 of the plate 20 sufficiently that the heads 110 of the bone screws 100 are below the recess 32 provided for the cam lock 40. The recess 32 of the cam lock 40 is a depression that allows the cam lock 40 to rest in the recess 32 and keep the profile below the exterior or outer surface 22 of the plate 20. Upon insertion of the fasteners 100 into the plate 20 and into the vertebral bodies, the cam locks 40 can be rotated such that the hemispherical or semicircular portion convex arcuate curvature 46 of the cam lock 40 covers or obstructs the bone fastener receiving opening 30 so that it turns and fits on an outer surface or upper portion of the bone fastener head 110. In doing so, the cam locks 40 provides a downward force and alternatively the fasteners 100 provide an upward force against the cam locks 40. The opposite side of each cam lock 40 has an appendage or arm 44 defined by a pair of opposing aligned concave arcuate curvatures 43 that mimic the shape of the bone fastener receiving holes 30 when the arm 44 is positioned in between the receiving holes 30 in the fully open position as shown in FIGS. 1-6. With this feature, it is important to note when the cam lock 40 is turned to the locked position and the force pushing against the fastener heads 110 is created, a tilting force is provided because the cam lock axis is off center between the transverse line intersecting the axis of the bone fastener receiving holes 30. This off-center feature enables the cam lock 40 to be slightly tilted or be provided with a biasing force that pushes the appendage or arm 44 against the floor or bottom of the recess 32. This feature is unique in that conventional cam locks have symmetrical loading about the bone fastener heads, either they hold 3 bone fasteners, or they provide 2 off the center axis of the cam lock typically aligned with a transverse line passing through a pair of bone fasteners.

The present invention is quite different in that it is designed to be biased off center from this transverse line in such a way that all the loads created form a biasing feature that creates a self-locking cam lock that is resistant to movement once installed providing assurances that the bone fasteners will not loosen as a result of backing out of the vertebral bodies.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A thoracolumbar plate assembly for engaging at least two vertebral bodies of a human spine along the anterior or lateral aspect of the spine comprises:
   a plate and at least two cam locks, said plate having a lower surface for contacting the vertebral bodies and an upper surface opposite to said lower surface, said plate assembly having a plurality of bone fastener receiving holes extending through said plate assembly from said upper surface to said lower surface;
   at least a first pair and second pair of said bone fastener receiving holes, the first pair being associated with a first of the vertebral bodies, the second pair being associated with a second of the vertebral bodies, and a recess associated with each of said at least first pair and second pair of said bone fastener receiving holes, said recess having a configuration for retaining one cam lock for locking at least two bone fasteners in each of said at least first pair and second pair of bone fastener receiving holes, the cam lock being pivotally rotatable about an axis in said recess and being offset from a transverse line passing through central longitudinal axes of each of said first or second pair of bone fastener receiving holes; and
wherein the cam locks in an open position do not cover the first pair or second pair of bone fastener holes allowing bone fasteners to be held in the bone fastener receiving holes and fastened to the vertebral bodies, wherein rotation of each of the cam locks to a closed position partially covering the bone fastener receiving holes applying a downward force locking against upper surfaces of heads of the pair of bone fasteners and the downward force tilts an opposite portion of the cam lock against a floor of the recess holding the cam lock in the closed position, and wherein each cam lock has an outer perimeter having one hemispherical or semicircular convex arcuate curvature and a pair of opposing aligned concave arcuate curvatures, wherein the convex arcuate curvature in a locked position partially covers two bone fastener receiving holes extending to the pair of opposing aligned concave arcuate curvatures, wherein the opposing aligned concave arcuate curvatures when positioned between a pair of bone fastener receiving holes does not cover the holes and has the curvature mimicking the shape of the bone fastener receiving holes, the opposite end of the cam lock is defined along the perimeter by concave surfaces forming an appendage or arm extending from the axis of each cam lock being tilted by the off axis positioning of load against the bottom surface of the recess holding the cam lock in a locked position, wherein a bone fastener with a head is inserted through each bone fastener receiving hole and each cam lock when moved in the closed and locked position has the hemispherical or semicircular convex arcuate portion partially covers and presses against two bone fastener heads creating a tilting force and the appendage or arm rotated toward a center portion of the plate and offset from the cam axis, the force causes the appendage or arm of the cam lock to tilt downwardly against a floor of the recess holding the cam lock in the locked position.

2. The plate assembly of claim 1 wherein the plate has curved upper and lower surfaces.

3. The plate assembly of claim 2 wherein the plate curved upper and lower surfaces have a high degree of curvature in a single radius of curvature, the curvature being greater than 1.5 mm.

4. The plate assembly of claim 3 wherein the high degree of curvature allows for the plate to better fit the lumbar anatomy due to the natural shape of the vertebra and lordosis of the spine.

5. The plate assembly of claim 1 wherein the plate assembly further comprises fasteners of various sizes along with temporary fixation pins which can be placed into the fastener holes to assist with placing of the plate.

6. The plate assembly of claim 5 wherein the fasteners are a self-drilling and self-tapping design to eliminate additional surgical steps in the operating room setting and have a variable angle to allow for better placement due to anatomy or previously implanted devices.

7. The plate assembly of claim 5 wherein bone fastener sizing is as follows: ç5.0 mm, ç5.5 mm, ç6.0 mm with threaded lengths of one of 25, 30, 35, 40, 45, 50, or 55 mm.

8. The plate assembly of claim 5 wherein each bone fastener uses a robust hexalobular drive feature to prevent stripping and have a strong connecting feature to a driver so as to prevent dropping into the wound cavity or off the sterile field.

9. The plate assembly of claim 1 wherein the plate sizing is as follows: 18 mm wide, with end to end lengths of one of 25, 30, 35, or 40 mm and 3 mm thick.

10. The plate assembly of claim 1 wherein diamond shaped teeth are located on the underside of each end of the lower surface of the plate to enhance grip to the bony surface.

11. The plate assembly of claim 1 wherein a central cavity is located in the center of the plate to allow for alignment with a guide wire or an additional fixation screw to secure the plate to an interbody device if desired.

12. The plate assembly of claim 1 wherein the plate assembly is configured as a thoracolumbar plate assembly which can be a lateral lumbar plate, anterior plate, posterior plate, lateral plate or lumbar plate.

* * * * *